(12) United States Patent
Son et al.

(10) Patent No.: US 9,926,331 B2
(45) Date of Patent: Mar. 27, 2018

(54) METHOD OF PREPARING ANHYDROSUGAR ALCOHOL USING ADDITIVE FOR PROHIBITING POLYMERIZATION BY DEHYDRATION

(71) Applicant: SK Innovation Co., Ltd., Seoul (KR)

(72) Inventors: Sung Real Son, Daejeon (KR); Sang Hye Shin, Daejeon (KR); In Hyoup Song, Daejeon (KR); Suk Joon Hong, Daejeon (KR); Tae Seung Kim, Yongin-si (KR); Yoon Jae Yim, Sejong-si (KR)

(73) Assignee: SK Innovation Co., Ltd., Seoul (KR)

( * ) Notice: Subject to any disclaimer, the term of this patent is extended or adjusted under 35 U.S.C. 154(b) by 0 days.

(21) Appl. No.: 15/406,073

(22) Filed: Jan. 13, 2017

(65) Prior Publication Data

US 2017/0204115 A1    Jul. 20, 2017

(30) Foreign Application Priority Data

Jan. 14, 2016    (KR) .......................... 10-2016-0004740

(51) Int. Cl.
    *C07D 493/04*    (2006.01)
(52) U.S. Cl.
    CPC .................. *C07D 493/04* (2013.01)
(58) Field of Classification Search
    CPC .................................................... C07D 493/04
    USPC .......................................................... 549/464
    See application file for complete search history.

(56) References Cited

U.S. PATENT DOCUMENTS 5,290,888 A * 3/1994 Gatechair ................ C07C 7/20
                                                                526/83

FOREIGN PATENT DOCUMENTS

KR     1020140048439 A    4/2014

OTHER PUBLICATIONS

Fleche et al., Starch/Starke 38 (1986) Nr. 1, S. 26-30.*

* cited by examiner

*Primary Examiner* — Taofiq A Solola
(74) *Attorney, Agent, or Firm* — The Webb Law Firm

(57) ABSTRACT

The present invention relates to a method for producing anhydrosugar alcohol using an organic additive having one hydroxyl group. The present invention makes it possible to prevent oligomers and polymers from being produced by polymerization of isosorbide during dehydration of sorbitol molecules, and thus solves problems, including a reduction in fluidity in a dehydration reactor, interference with the flow of fluids in the reactor and pipelines, and interference with stirrer operation, which occur due to the oligomers and polymers.

9 Claims, No Drawings

METHOD OF PREPARING ANHYDROSUGAR ALCOHOL USING ADDITIVE FOR PROHIBITING POLYMERIZATION BY DEHYDRATION

CROSS-REFERENCE TO RELATED APPLICATION

This application claims priority to Korean Patent Application No. 10-2016-0004740 filed Jan. 14, 2016, the disclosure of which is hereby incorporated in its entirety by reference.

TECHNICAL FIELD

The present invention relates to a method of preparing anhydrosugar alcohol using an additive for prohibiting polymerization by dehydration, and more particularly, to a method of producing anhydrosugar alcohol by dehydration of sugar alcohol, the method comprising a step of adding an organic compound, which contains one hydroxyl group, as an additive for prohibiting polymerization by dehydration.

BACKGROUND ART

Due to the exhaustion of traditional energy sources together with an increase in the global energy demand, impetus is currently being given to the development of alternative energy sources. Among them, biomass is a renewable quantitative biological resource that attracts a great deal of attention.

Among biomass-based industrial raw materials, isosorbide ($C_6H_{10}O_4$) that is prepared by dehydration of sorbitol ($C_6H_{14}O_6$) under acid catalyst conditions attracts attention as an environmentally friendly raw material for preparing polycarbonate (PC) as a substitute for bisphenol A (BPA), an epoxy monomer or an environmentally friendly plasticizer.

A reaction that converts sorbitol to isosorbide is a dehydration reaction that removes two water molecules from sorbitol in the presence of an acid catalyst. During dehydration of sorbitol molecules, oligomers and polymers can be produced by polymerization of a reaction intermediate, side-reaction products or isosorbide, and such polymers are carbonized during an additional dehydration process at high temperature to form carbonized materials. The carbonized materials reduce fluidity in the dehydration reactor while becoming solid. Finally, the carbonized materials become a solid having no fluidity, interfere with the flow of fluids in the reactor and pipelines, and also interfere with stirrer operation.

Among compounds formed by side reactions, a dihydrofuran compound is expected to be a major compound that is likely to cause polymerization. To prevent dehydration polymerization from being caused by the dihydrofuran compound, compounds having an alcohol group and compounds having an amide or thiol group, which may have an action similar to that of the alcohol group-containing compounds, are contemplated as additives that bond with the dihydrofuran compound to terminate the reaction.

Korean Patent Publication No. 2014-0048439 discloses a method for producing anhydrosugar alcohol, which comprises a step of converting hydrogenated sugar to anhydrosugar alcohol by a dehydration reaction and which is carried out in the presence of a polyol, such as ethylene glycol, polyethylene glycol, polypropylene glycol, glycerol or the like, as a reaction diluent in the dehydration reaction. However, because a reaction for producing isosorbide is generally carried out at high temperature under a vacuum, a high-boiling-point compound which is not volatilized under the reaction conditions should be added during the reaction. In addition, if the compound added has several functional groups such as alcohol groups, there will be a problem in that additional dehydration reactions in addition to the production of a reaction intermediate occur depending on reaction conditions, and for this reason, the yield of anhydrosugar alcohol is reduced.

Accordingly, the present inventors have found that, when a high-boiling-point compound, which is not volatilized under reaction conditions and has one alcohol group, is added during dehydration of sorbitol molecules in order to solve the problems that carbonized materials derived from oligomers or polymers, produced by polymerization of a reaction intermediate, side-reaction products or isosorbide during the dehydration, reduce fluidity in the dehydration reactor while becoming solid, interfere with the flow of fluids in the reactor and pipelines and also interfere with stirrer operation, it can inhibit the polymerization during dehydration to inhibit the production of the carbonized materials, thereby completing the present invention.

SUMMARY OF INVENTION

It is an object of the present invention to provide an effective method for producing anhydrosugar alcohol, which overcomes the problems that carbonized materials derived from oligomers or polymers, produced by polymerization of a reaction intermediate, side-reaction products or isosorbide during dehydration of sorbitol molecules, reduce fluidity in the dehydration reactor while becoming solid, interfere with the flow of fluids in the reactor and pipelines and also interfere with stirrer operation.

DETAILED DESCRIPTION OF THE INVENTION

To achieve the above objects, the present invention provides a method of producing anhydrosugar alcohol by dehydration of sugar alcohol, the method comprising a step of adding an organic compound, which contains one hydroxyl group, as an additive for prohibiting polymerization during the dehydration.

BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein and the experiment methods, which will be described below, are those well-known and commonly employed in the art.

The present inventors have found that, when a high-boiling-point compound having one alcohol group is added during a process for producing anhydrosugar alcohol, it can prohibit polymerization by dehydration to thereby suppress the production of carbonized materials in a reactor.

Therefore, in one aspect, the present invention is directed to a method of preparing anhydrosugar alcohol by dehydration of sugar alcohol, comprising a step of adding R—OH (R: organic group) which comprises one hydroxyl group and has a boiling point of 100° C. or higher, as an additive for prohibiting polymerization during the dehydration.

Sorbitol is converted to isosorbide by a two-step dehydration process. 1,4-sorbitan or 3,6-sorbitan, which is an intermediate produced in the first dehydration step of the process, can form a dihydrofuran compound by side reactions. The dihydrofuran compound is highly reactive, is polymerized with the surrounding sorbitan, and still has a dihydrofuran ring even after polymerization to cause additional side reactions. Thus, an additive compound, which is added to terminate this reaction and bonds with reaction active sites to prevent an additional reaction from occurring, is preferably a compound having an alcohol group (hydroxyl group) without having other dehydration reaction active sites. Thus, the additive compound is preferably a compound having one alcohol group. Specifically, the additive compound is a high-boiling-point alcohol which is maintained in a liquid state at high temperature under a vacuum.

In order for the additive compound to have a high boiling point, the additive compound may further contain a long-chain hydrocarbon group (linear or branched), a ketone group, an ether group, an ester group or a carboxylic group.

A boiling point of the high-boiling-point alcohol of the present invention may be 100° C. or higher, and may preferably range from 100° C. to 350° C.

Specifically, in the present invention, R in the organic compound R—OH is an organic group which may be a linear or branched alkyl group having 8 or more carbon atoms, preferably 8 to 24 carbon atoms, more preferably 12 to 24 carbon atoms. Thus, the additive for prohibiting polymerization by dehydration, which is used in the production of anhydrosugar alcohol according to the present invention, is most preferably an aliphatic alcohol having 12 to 24 carbon atoms.

In addition, the additive for prohibiting polymerization by dehydration for the production of anhydrosugar alcohol according to the present invention may comprise a ketone group, an ether group, an ester group, or a carboxylic group.

An alcohol having the ether group according to the present invention is preferably poly(ethylene glycol)alkyl ether, poly(ethylene glycol)alkyl phenyl ether, or poly(ethylene glycol)alkyl cyclohexyl ether. The alkyl group may have 1 to 12 carbon atoms and preferably may be a methyl group, an ethyl group, a propyl group, an isopropyl group, or a butyl group, but is not limited thereto.

In addition, the alcohol group may be located at the terminal end (primary) or the chain.

In addition, R in the organic compound R—OH may further comprise amide, thiol or phosphine, which can induce a reaction similar to that induced by the alcohol group.

In another aspect, the present invention is directed to a method of producing anhydrosugar alcohol by dehydration of sugar alcohol, the method comprising a step of adding an organic compound, which contains any one selected from the group consisting of amide, thiol and phosphine groups, and has a boiling point of 100° C. or higher, as an additive for prohibiting polymerization by the dehydration.

The organic compound may further comprise an alcohol group.

In the production method of the anhydrosugar alcohol according to the present invention, the dehydration of the sugar alcohol may be performed at a pressure of 0.01-50 mmHg and a temperature of 100-250° C.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

70 g of D-sorbitol (Aldrich) was fed into a 250 mL round bottom flask and dissolved at 110° C., and then 3.0 wt % of naphthalenesulfonic acid hydrate (Aldrich) and 5.0 wt % of poly(ethylene glycol) methyl ether (molecular weight: 1,000; TCI) were added thereto, followed by stirring under a reaction pressure of 5-10 mmHg. Such conditions were maintained for 100 minutes, after which the reaction temperature was elevated to 200° C. so that the produced isosorbide would be evaporated and discharged through the reactor top. The yield of the isosorbide thus obtained was 62.53 wt % relative to the amount of the feed sorbitol.

Example 2

The production of isosorbide from sorbitol was performed in the same manner as described in Example 1, except that 5.0 wt % of Triton™ X-100 (a surfactant based on poly(ethylene glycol) tert-octylphenyl ether; Aldrich) was used instead of poly(ethylene glycol) methyl ether. The yield of the isosorbide thus obtained was 62.95 wt %.

Example 3

To measure the degree of carbonization of residue remaining in the flask after the production of isosorbide as described in Example 1, elementary analysis was performed. The number of moles of hydrogen per mole of carbon in the residue was 1.14.

Example 4

To measure the degree of carbonization of residue remaining in the flask after the production of isosorbide as described in Example 2, elementary analysis was performed. The number of moles of hydrogen per mole of carbon in the residue was 1.20.

Example 5

Poly(ethylene glycol)methyl ether was used in an amount of 13.8 wt % in the production process of isosorbide as described in Example 1. After reaction, elementary analysis was performed to measure the degree of carbonization of residue remaining in the flask. The number of moles of hydrogen per mole of carbon in the residue was 1.52.

Comparative Example 1

The production of isosorbide from sorbitol was performed in the same manner as described in Example 1, except that 5.0 wt % of poly(ethylene glycol) (molecular weight: 1,000; Aldrich) was used instead of poly(ethylene glycol) methyl ether. The yield of the isosorbide thus obtained was 61.50 wt %.

Comparative Example 2

The production of isosorbide from sorbitol was performed in the same manner as described in Example 1, except that 5.0 wt % of poly(ethylene glycol) (molecular weight: 3,000;

Aldrich) was used instead of poly(ethylene glycol) methyl ether. The yield of the isosorbide thus obtained was 59.56 wt %.

Comparative Example 3

To measure the degree of carbonization of residue remaining in the flask after the production of isosorbide as described in Comparative Example 1, elementary analysis was performed. The number of moles of hydrogen per mole of carbon in the residue was 1.07.

From Examples 1 and 2 and Comparative Examples 1 and 2 as described above, it could be seen that, when the additive for preventing carbonization was added during the process of producing anhydrosugar alcohol by dehydration of sugar alcohol, the yield of anhydrosugar alcohol was higher in the case in which the compound containing one alcohol group per molecule was used (Examples 1 and 2) than in the case in which the polyol containing a larger number of alcohol groups (Comparative Examples 1 and 2), because polymerization during dehydration in Examples 1 and 2 was prevented. Furthermore, it is expected that amide, thiol or phosphine, which can induce a reaction similar to that induced by the alcohol group, will show a high production yield of anhydrosugar alcohol while inhibiting side reactions through the same action as that of the alcohol group. In addition, from Examples 3-5 and Comparative Example 3, it could be seen that, when the additive was added, the number of moles of hydrogen per mole of carbon was large, indicating that polymerization during dehydration was inhibited and carbonization by the polymerization was inhibited. Because such results are those measured for the residue in the state in which isosorbide did not substantially remain in the reactor and in which the reaction was terminated at high temperature, it is expected that the actual ratio of hydrogen/carbon will further increase. Through the Examples and Comparative Example as described above, it was found that, when the additive according to the present invention is added during the process of producing anhydrosugar alcohol by dehydration of sugar alcohol, it can show a high production yield of anhydrosugar alcohol while having the effect of inhibiting carbonization.

INDUSTRIAL APPLICABILITY

The method for producing anhydrosugar alcohol according to the present invention makes it possible to prevent oligomers and polymers from being produced by polymerization of a reaction intermediate, side-reaction products or isosorbide during dehydration of sorbitol molecules, and thus solves problems, including a reduction in fluidity in a dehydration reactor, interference with the flow of fluids in the reactor and pipelines, and interference with stirrer operation, which occur due to the oligomers and polymers.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method of preparing anhydrosugar alcohol by dehydration of sugar alcohol, the method comprising a step of adding R—OH (R: linear or branched alkyl group having carbon atoms of at least 8) which comprises one hydroxyl group and has a boiling point of 100° C. or higher, as an additive for prohibiting polymerization by the dehydration.

2. The method of claim 1, wherein the additive for prohibiting polymerization by the dehydration is an aliphatic alcohol having 12 to 24 carbon atoms.

3. A method of preparing anhydrosugar alcohol by dehydration of sugar alcohol, the method comprising a step of adding R—OH (R: a ketone group, an ether group, an ester group, or a carboxylic group) which comprises one hydroxyl group and has a boiling point of 100° C. or higher, as an additive for inhibiting polymerization during the dehydration.

4. The method of claim 3, wherein the additive for prohibiting polymerization by the dehydration is poly(ethylene glycol)alkyl ether, poly(ethylene glycol)alkyl phenyl ether or poly(ethylene glycol)alkyl cyclohexyl ether.

5. The method of claim 4, wherein the alkyl has 1 to 12 carbon atoms.

6. The method of claim 1, wherein the dehydration of the sugar alcohol is performed at a pressure of 0.01-50 mmHg and a temperature of 100-250° C.

7. A method of producing anhydrosugar alcohol by dehydration of sugar alcohol, the method comprising a step of adding an organic compound which comprises any one selected from the group consisting of amide and thiol and has a boiling point of 100° C. or higher, as an additive for prohibiting polymerization by the dehydration.

8. The method of claim 7, wherein the organic compound further comprises an alcohol group.

9. The method of claim 7, wherein the dehydration of the sugar alcohol is performed at a pressure of 0.01-50 mmHg and a temperature of 100-250° C.

* * * * *